Figure 1:
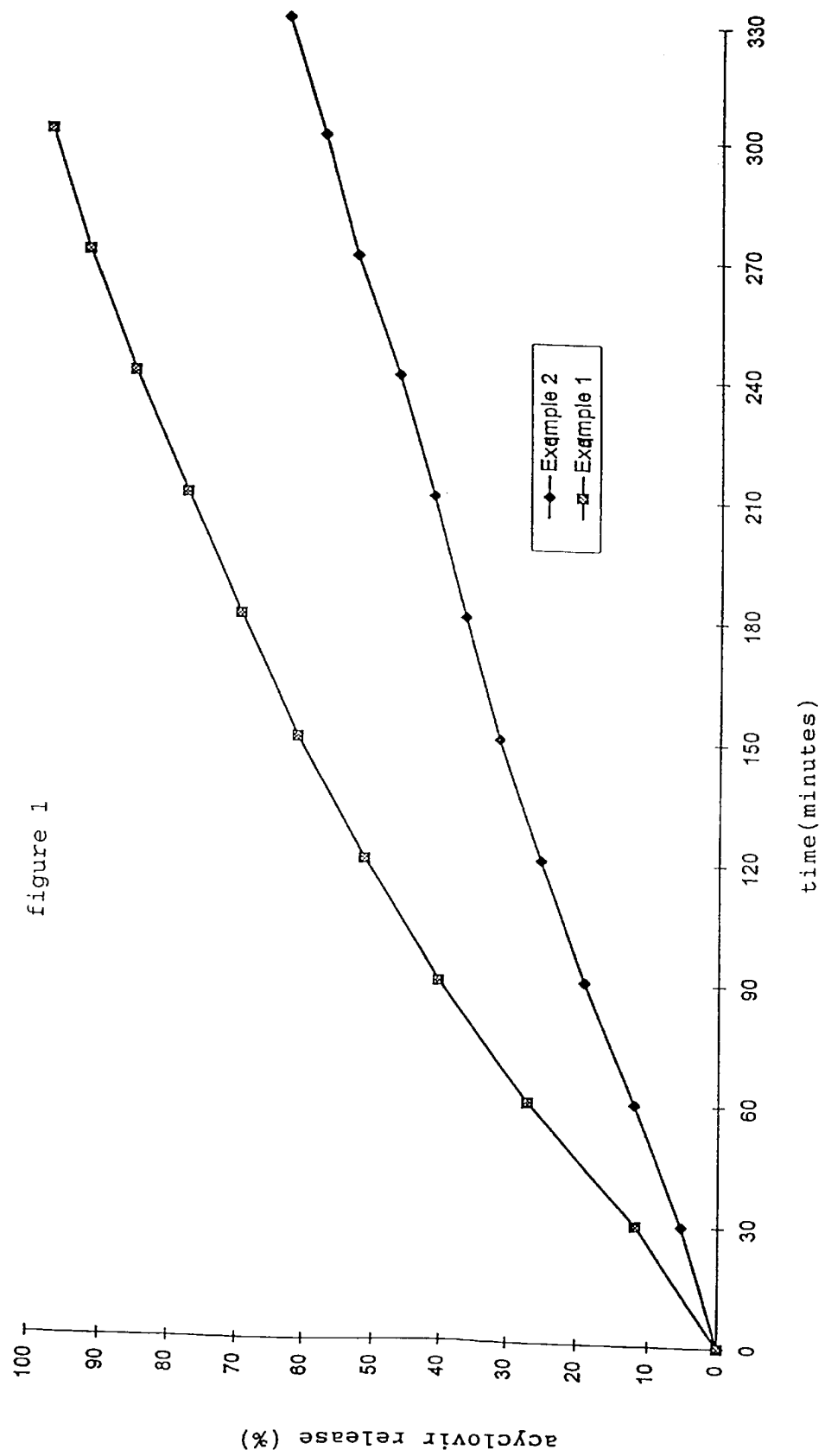

United States Patent [19]
Seth et al.

[11] Patent Number: 6,048,547
[45] Date of Patent: Apr. 11, 2000

[54] PROCESS FOR MANUFACTURING SOLID COMPOSITIONS CONTAINING POLYETHYLENE OXIDE AND AN ACTIVE INGREDIENT

[76] Inventors: Pawan Seth, 10 Meryton, Irvine, Calif. 92612; Andre Stamm, 33a rue des Olives, 67870 Griesheim, France

[21] Appl. No.: 09/120,914

[22] Filed: Jul. 22, 1998

Related U.S. Application Data

[63] Continuation-in-part of application No. 08/943,304, Oct. 14, 1997, which is a continuation of application No. PCT/FR96/00574, Apr. 15, 1996.

[51] Int. Cl.[7] ................................................... A61K 9/14
[52] U.S. Cl. ............................................ 424/464; 424/465
[58] Field of Search ..................................... 424/464, 465

[56] References Cited

U.S. PATENT DOCUMENTS

| | | |
|---|---|---|
| 5,037,653 | 8/1991 | Dawson . |
| 5,273,758 | 12/1993 | Royce . |
| 5,354,560 | 10/1994 | Lovrecich ........................... 424/489 |
| 5,654,005 | 8/1997 | Chen et al. . |
| 5,766,623 | 6/1998 | Ayres et al. . |

FOREIGN PATENT DOCUMENTS 0 232 877 A2   8/1987   European Pat. Off. .

OTHER PUBLICATIONS

International Preliminary Examination Report of PCT/FR96/00574.

"Poly(ethylene oxide) (PEO) and Different Molecular Weight PEO Blends Monolithic Devices for Drug Release", A. Apicella, B. Cappello, M.A. Del Nobile, M.I. La Rotonda, G. Mensitieri and L. Nicolais, *Biomaterials*, 1993, pp. 83–90.

*Primary Examiner*—James H. Reamer
*Attorney, Agent, or Firm*—Harness, Dickey & Pierce, P.L.C.

[57] ABSTRACT

Methods for the preparation of solid compositions are disclosed, where the composition comprises an active ingredient in association with polyethylene oxide and conventional additives, excluding basic compounds. Such compositions are suitable for use as pharmaceutical compositions.

18 Claims, 1 Drawing Sheet

PROCESS FOR MANUFACTURING SOLID COMPOSITIONS CONTAINING POLYETHYLENE OXIDE AND AN ACTIVE INGREDIENT

This application is a continuation-in-part of prior application Ser. No. 08/943,304, filed Oct. 14, 1997, which is a continuation of PCT patent application Ser. No. PCT/FR96/00574, filed Apr. 15, 1996.

The present invention relates to novel solid compositions, notably pharmaceutical compositions, containing polyethylene oxide and an active ingredient, and to methods for their preparation.

Certain medicaments need to be formulated in so-called delayed-release or sustained release form.

Polyethylene oxide referred to as PEO below is moreover known as a component of medicaments in tablet form designed to be administered by oral route. This compound is marketed by the Union Carbide corporation under the commercial name Polyox. The use of PEO for formulating medicaments has furthermore been the subject matter of many earlier patents.

EP-A-0 277 092, in the name of Ciba-Geigy relates to a composition comprising a casing in a material that is porous to water but not to the active ingredient, surrounding a central core consisting of a mixture of a substance that is weakly soluble in water, and a hydrophilic swelling material, said material consisting of a mixture of PEO and a vinyl pyrrolidone/vinyl acetate polymer. The composition in that patent is an example of current compositions in which a core which swells when exposed to water is surrounded by a water-porous material, release of the active ingredient being delayed or sustained as a result of the time necessary to expand the core, and for diffusion to take place through the casing following the penetration of water.

The abstract of the U.S. Pat. No. 4,404,183 and U.S. Pat. No. 4,343,789 discloses two embodiments of a sustained release composition. In the first embodiment, the composition contains PEO, the active ingredient in an amorphous form, and a basic component. In the second embodiment, the active ingredient is nicardipine in an amorphous state, it being possible to omit the basic component.

Actually, the compositions according to the prior art are complex, require specific active ingredients or are provided in a specific form. Moreover, the results achieved are not always very good.

The present invention provides a simple composition which is suitable for use with a multiplicity of active ingredients, and has a remarkable delaying or sustaining effect.

Thus, the present invention provides a solid composition comprising, by weight based on the total weight of the composition:
(a) from 1 to 70% of an active ingredient which is not in an amorphous form;
(b) from 1 to 95% of polyethylene oxide;
(c) the balance consisting of conventional additives, excluding basic components.

The expression "solid composition" means that the composition is in a tablet or mini-tablet form, these in their turn being able to be encapsulated using for example the conventional hard gelatin.

The expression "active ingredient" should be understood in its normal sense and, generally speaking, covers medicaments for treatment of the human or animal body as well as an association of one or several such medicaments. Active ingredients that are either hydrophilic or lipophilic are envisaged.

The expression "not in amorphous form" should be understood in its conventional meaning. Various sources give a definition of this term "amorphous" as meaning non-crystalline, lacking the lattice structure characterizing the crystalline state. The following references, which provide a definition of the term amorphous (or the opposite thereof) are, in a on-limiting manner: Hawley's Condensed Chemical Dictionary, 12th Edition, p. 71; Handbook of Chemistry and Physics, 65th Edition, F-67; The Theory and Practice of Industrial Pharmacy, 1970, pp. 253–255; Remington's Pharmaceutical Sciences, 14th Edition, p. 182; General Chemistry 1992, pp.314–315; Encyclopedia of Pharmaceutical Technology, vol I, pp. 12–13.

The expression "excluding basic compounds" should be understood as excluding the presence of a compound or a group of compounds that confer a basic nature on the composition, in other words a pH greater than 7, when the composition is diluted in water at a rate of 10 g per liter of water. In particular, this term should be taken as excluding the presence of one or several basic component(s) such as described in column 1, lines 38 to 62 of US-A-4,404,183 if no acid compound is counteracting the effect of said basic compound, or if the basic compound is present in a relatively large amount.

According to one preferred embodiment, the composition according to the invention, comprises:
(a) from 5 to 45% of an active ingredient;
(b) from 25 to 70% polyethylene oxide
(c) the balance consisting of conventional additives, excluding basic components.

According to one preferred embodiment of the composition according to the invention, the active ingredient is a hydrophilic or lipophilic active ingredient, advantageously a hydrophilic ingredient.

According to another preferred embodiment of the composition according to the invention, the active ingredient is selected from the group comprising acyclovir, nifedipine, nicardipine, captopril, verapamil, diltiazem, oxybutynine, valacyclovir, glipizide, felodipine, isosorbide, carbidopa, levodopa, pentoxiphylline, and their pharmaceutically acceptable salts.

According to one alternative embodiment, in the composition according to the invention, the polyethylene oxide has a molecular weight which varies from 50,000 to 8,000,000, and preferably from 100,000 to 3,000,000. The required molecular weight for the PEO can be obtained by mixing PEO of differing molecular weights, that are available commercially.

According to a further embodiment, in the composition according to the invention, the balance consisting of conventional additives comprises microcrystalline cellulose, lactose, ascorbic acid, pigments, plasticizing agents, lubricants and so on. Obviously, other conventional additives known to those skilled in the art can be employed.

According to one embodiment of the invention, in a composition, the balance consisting of conventional additives comprises magnesium stearate and/or glycerol behenate and/or sodium stearyl fumarate, which is employed as a lubricant ensuring better compression of the composition when provided in tablet form, for example.

According to one or alternative embodiment, the composition is additionally coated. Surface coating is employed for the purposes of improving appearance making the drug more readily acceptable to the patient, or for dimensionally stabilizing the compressed tablet. The coating can be a conventional coating suitable for enteral use. It is obtained using any conventional technique employing conventional ingredients. A surface coating can for example be obtained using a quick-dissolving film. It should be noted that the coating according to this invention is fundamentally different from the coating used in EP-A-0,277,092 as one does not encounter, in the invention, the dichotomy (water-swellable core)/(water-porous coating), and moreover, the coating in the invention dissolves and/or disintegrates whereas the coating in EP-A-0,277,092 does not dissolve.

The present solid compositions are suitable for the administration of medicaments. Thus, the invention also relates to pharmaceutical compositions deriving therefrom as well as to compositions thereof for use as medicaments.

The present composition can be obtained by any conventional method known to those skilled in the art such as, for example direct compression after simply mixing the dry ingredients, moist or wet granulation involving the use of a granulation liquid, and dry granulation involving a densification phase for the dry mixture.

However, use is preferably made of a process comprising the steps of:

(i) mixing in the dry state and for a sufficient time, the active ingredient, polyethylene oxide and optionally, one or several additives;

(ii) optionally adding solvent when this is used, followed by mixing for a sufficient period of time;

(iii) granulation by passage through a suitable sieve;

(iv) drying the granules thus formed for a sufficient period of time;

(v) optionally adding one of more additives, with mixing in the dry state for a sufficient time and passage through a suitable sieve;

(vi) optionally adding one or several additives and mixing in the dry state for a sufficient period of time;

(vii) compressing the mixture obtained from the preceding steps to obtain the desired compressed tablet; and (viii) optionally coating said compressed tablet.

The solvent employed, when use is made of a solvent, is preferably an alcohol. The solvent is eliminated by drying at one point or another in the process, and is substantially not encountered in the final composition.

The choice of mixing times, apparatus used, sieve mesh, and other operating conditions are within the province of the normal knowledge of those skilled in the art.

The invention will now be described in more detail, with reference to FIG. 1 which shows percentage in-vitro release of an active ingredient as a function of time for the solid compositions of examples 1 and 2.

Without wishing to be bound by any theory, the applicant believes that the PEO, in the formulation, forms a hydrogel from contact with water. This hydrogel dissolves more or less rapidly as a function of the molecular weight of the PEO employed. Choosing the molecular weight of the PEO, in combination with a suitable choice of the weight concentrations of the active ingredient, of PEO, and of additives enables release of the active ingredient to be controlled.

Moreover, the present composition exhibits particularly surprising results. In a hydrophilic matrix, when the concentration of the hydrophilic active ingredient increases, one would expect that the rate of release of the active ingredient would increase. The present composition exhibits the opposite effect, in the case, for example, of acyclovir as active ingredient. This is clearly shown in FIG. 1, which gives in-vitro dissolution of the compositions of examples 1 and 2. The composition of example 1 has a lower concentration of the active ingredient (200 mg medicament in a 905 mg tablet) and shows a faster in-vitro release of the drug as compared to the formulation of example 2 which has a higher concentration of the active ingredient (400 mg of medicament in a 905 mg tablet). This result is particularly surprising.

The carrying out of the process as depicted above with water as the wetting liquid is difficult. Indeed, PEO is a water-swellable polymer which instantaneously forms agglomerates when it comes into contact with the droplets of water. This leads to the final formation of elastic lumps within the heart of the mass to be granulated, these being difficult to size, notably on an oscillating granulation grid.

The instant improved process is thus a method for wet granulation of PEO, using water as the wetting liquid. It is now possible to avoid both the problems linked to direct compression (the heterogeneous nature of the mixture) as well as problems associated with organic solvents (cost, inflammability, toxicity towards the operator and the environment).

The improved process consists in a two-stage wetting allowing PEO to be hydrated without forming lumps. During the first wetting step, aqueous wetting of the active ingredient alone is carried out or, if appropriate, of the active ingredient and one or several excipients such as, for example, microcrystalline cellulose or lactose. During the second wetting step, the PEO is added to the foregoing wet mixture. These two wetting steps are both simply referred to as the "wetting step" herein.

The wetting liquid can if necessary include substances in solution in order to modify the properties of the granulated product, and to improve the wetting operation. Thus, binders such as hydroxypropylmethyl cellulose or polyvinylpyrrolidone can be employed in order to improve the properties of the granulated product. When such substances are used, their concentration can vary up to about 20%, for example between 1 and 10%.

It is important to note that in all cases, water constitutes substantially the only solvent of the wetting liquid in the improved process.

The wetting operation can be carried out in any conventional blender described in the literature such as for example apparatus manufactured by Vector, Moritz, Collette, Bouvard, Lodige, etc. Such blenders can employ kneading, blades, planetary arrangements or, preferably but not obligatorily, high speed with or without a lump-breaking knife. Wetting takes place for a period comprised between 0,5 and 15 min, for example between 2 and 6 min.

Preferably, but not indispensably, slight "over-wetting" of the powders is done which renders the following operations easier more easy. "Over-wetting" should be taken to mean "adding liquid in excess to the amount required to agglomerate the powder mixture".

The excess water added during the possible slight overwetting in the first step improves agglomeration of the PEO to the active ingredient and, if present, to the other excipients present.

For example, the weight ratios water/composition or water/PEO may vary respectively from 0.13 to 0.36 and 0.18 to 0.5.

Once the first wetting step has been performed, the PEO is added into the apparatus and a supplementary mixing is performed thereby achieving supplementary wetting of the PEO. During this second mixing, the PEO gets integrated into the granulated product and swells slightly. However, surprisingly, there is no formation of lumps or clods, contrary to what is obtained in conventional granulation, using one single step, as described in the literature.

This last operation can be carried out in the same mixer as was used for the first step, or any other conventional blender as described above. The mixing time is comprised between 0,5 and 15 min, for example between 2 and 6 min.

The process includes other steps which are conventional in the art.

One prior step in which the active ingredient is intimately mixed with the additives, when present, can be provided.

A granulation step notably is carried out after incorporation and mixing of the PEO. This granulation step can be done on a screen having a suitable mesh size.

A drying step, notably using a fluidized bed or a drying oven, is also implemented, notably following the granulation step. The drying step is considered as having been carried out when the residual water content is below 10%, for example below 3%, depending on the kind and amount of ingredients.

Steps in which additives are added and blended can be included, if necessary.

A step in which the granules, notably dry granules, are size-graded can be provided. Size grading is carried out also on a screen having a mesh size comprised for example between 100 and 1000 µm.

Final compression steps and, optionally, tablet coating steps are also provided. Notably, a step in which a compression additive is added can be provided after drying, but prior to compression. These final compression steps are obviously not necessary for preparing capsules enclosing the granules.

It is clear that the above order for the steps, apart from that of wetting, is not fixed; one could for example add the compression additives right at the beginning or immediately following addition of the PEO. Similarly, a granulation step could optionally be carried out before adding the PEO.

Choice of the duration of mixing, the apparatus, the screens and other operating conditions is a matter for the normal skill and judgement of the person skilled in the art.

The improved process is thus a process for preparing a solid pharmaceutical composition comprising, by weight based on the total weight of the composition:

(a) from 1 to 70% of active ingredient which is not in an amorphous form;

(b) from 10 to 95% of polyethylene oxide;

(c) the balance consisting of conventional additives, comprising the steps of:

(i) mixing said active ingredient and optionally one or several additives with an aqueous solution for a sufficient period of time; then (ii) adding the PEO, and mixing for a sufficient period of time.

According to one embodiment, step (i) of mixing with the aqueous solution is carried out in the presence of excess liquid.

According to another embodiment, said aqueous solution consists of water, and, optionally, water-soluble additives.

According to yet another embodiment, the improved process further comprises a granulation step.

According to yet another embodiment, the improved process further comprises a granulation step; said granulation step can be carried out on a screen of suitable mesh size.

According to yet another embodiment, the improved process additionally comprises a drying step.

According to yet another embodiment, the improved process additionally comprises a compression step; said compression step can be preceded by a step in which additives are added and blended.

A specific embodiment of the instant improved process is a process comprising the steps of:

(i) mixing, for a sufficient period of time, active ingredient and, optionally, one of several additives, with said aqueous solution; then (ii) adding PEO and mixing for a sufficient period of time;

(iii) granulating the mixture obtained from step (ii);

(iv) drying granules thus formed for a sufficient period of time;

(vi) optionally, adding one or several additives, and mixing in the dry state for a sufficient period of time;

(vii) compressing the mixture obtained from the preceding step into a tablet.

Preferably, step (i) of mixing with the aqueous solution is carried out in the presence of excess liquid.

The examples below are provided as examples illustrating the invention and should not be considered as limiting its scope. In the examples, the amount of solvent employed is given in brackets, it being understood that the solvent is substantially absent in the final composition. In the examples, tablet hardness is measured using a Schleuniger 4M hardness tester.

EXAMPLE 1

The following composition was prepared:

| | |
|---|---|
| Acyclovir | 200.0 mg |
| PEO (MW = 100 000) | 700.0 mg |
| Magnesium stearate | 5.0 mg |
| Industrial alcohol | (260.0 mg) |

The acyclovir and PEO are weighed and added to a mixer kneader. Mixing in the dry state is performed for 5 minutes. Alcohol is added to the mixture and followed by mixing by 5 minutes. Granulation is achieved by passing through a sieve of 1.6 mm mesh. The granules are dried and are passed through a 0.8 mm mesh sieve. After weighing, the magnesium stearate is added and mixing in the dry state is performed during 2 minutes. Tablets are obtained by compression using a Frogerais MR 15 machine.

EXAMPLE 2

The following composition is prepared:

| | |
|---|---|
| Acyclovir | 400.0 mg |
| PEO (MW = 100 000) | 500.0 mg |
| Magnesium stearate | 5.0 mg |
| Industrial alcohol | (260.0 mg) |

The acyclovir and PEO are weighed and added in a mixer kneader. Mixing in the dry state is performed for 5 minutes. Alcohol is added to the mixture and followed by mixing by 5 minutes. Granulation is achieved by passing through a sieve of 1.6 mm mesh. The granules are dried and are passed through a 0.8 mm mesh sieve. After weighing, the magnesium stearate is added and mixing in the dry state is performed during 2 minutes. Tablets are obtained by compression using a rotary Frogerais MR 15 type machine.

EXAMPLE 3

The following composition was prepared:

| | |
|---|---|
| Nifedipine | 60.0 mg |
| Microcristalline cellulose | 100.0 mg |

-continued

| | |
|---|---|
| PEO (MW = 3 000 000) | 336.0 mg |
| Colloidal silicon dioxide | 2.5 mg |
| Magnesium stearate | 2.5 mg |
| Industrial alcohol | (150.0 mg) |

The nifedipine, microcrystalline cellulose (available from the company FMC under the commercial name Avicel PH 101) and the PEO are weighed and added to a mixer kneader. They are mixed in the dry state for 5 minutes and the alcohol is added to the mixture with further mixing for 5 minutes. Granulation is performed by passage through a 1.8 mm mesh sieve. The granules are dried. The colloidal silicon dioxide (available from Degussa under the commercial name Aerosil 200) is weighed and added and mixing is carried out in the dry state for 5 minutes followed by passage through a 0.6 mm mesh sieve. The magnesium stearate is weighed and added with mixing in the dry state for 2 minutes. The tablets are obtained by compression in a rotary Frogerais MR 15 type machine.

EXAMPLE 4

| Core | |
|---|---|
| Nifedipine | 60.0 mg |
| Microcristalline cellulose | 100.0 mg |
| PEO (MW = 3 000 000) | 336.0 mg |
| Colloidal silicon dioxide | 2.5 mg |
| Magnesium stearate | 2.5 mg |
| Industrial alcohol | (150.0 mg) |
| Coating: | |
| Iron oxide | 2.0 mg |
| Titanium dioxide | 1.0 mg |
| Methylcellulose | 12.0 mg |
| Industrial alcohol | (150.0 mg) |

The nifedipine, microcrystalline cellulose (available from the company FMC under the commercial name Avicel PH 101) and the PEO are weighed and added to a mixer kneader. They are mixed in the dry state for 5 minutes and the alcohol is added to the mixture with further mixing for 5 minutes. Granulation is performed by passage through a 1.6 mm mesh sieve. The granules are dried. The colloidal silicon dioxide (available from Degussa under the commercial name Aerosil 200) is weighed and added and mixing is carried out in the dry state for 10 minutes followed by passage through a 0.8 mm mesh sieve. The magnesium stearate is weighed and added with mixing in the dry state for 2 minutes. The tablets are obtained by compression in a rotary Frogerais MR 15 type machine.

Following this, the methylcellulose (available from Colorcon under the commercial name Methocel) is dissolved in the alcohol. The iron oxide and titanium dioxide are added to the solution, followed by homogenization in an Ultra Turrax apparatus for 10 minutes. The tablets are coated by spraying this suspension in a perforated pan coating apparatus of the "Glatt coater" type.

EXAMPLE 5

The following composition is prepared:

| Core: | |
|---|---|
| Nicardipine.HCl | 60.0 mg |
| Microcrystalline cellulose | 77.0 mg |
| PEO (MW = 2 000 000) | 270.0 mg |
| Magnesium stearate | 3.0 mg |
| Industrial alcohol | (150.0 mg) |
| Coating: | |
| Iron oxide | 2.0 mg |
| Titanium dioxide | 1.0 mg |
| Methylcellulose | 12.0 mg |
| Industrial alcohol | (150.0 mg) |

The nicardipine.HCl, microcrystalline cellulose (Avicel PH 101) and PEO are weighed and added to a kneader. Mixing in the dry state is carried out for 5 minutes. The alcohol is added to the mixture with further kneading for 5 minutes. Granulation is carried out by passage through a 1.6 mm mesh sieve. The granules are dried and passed through a 0.8 mm mesh sieve. The magnesium stearate is weighed and added followed by dry mixing for 2 minutes. The tablets are obtained by compression in a rotary Frogerais MR 15 type machine.

Following this, the methylcellulose (Methocel) is dissolved in the alcohol. The iron oxide and titanium oxide are added to the solution followed by homogenization in an Ultra Turrax apparatus for 10 minutes. The tablets are coated by spraying this suspension in a Glatt coater type coating apparatus.

EXAMPLE 6

The following composition is prepared:

| Core: | |
|---|---|
| Captopril | 50.0 mg |
| Microcrystalline cellulose | 100.0 mg |
| PEO (MW = 2 500 000) | 300.0 mg |
| Ascorbic acid (powder) | 100.0 mg |
| Magnesium stearate | 3.0 mg |
| Coating: | |
| Titanium dioxide | 1.0 mg |
| Methylcellulose | 10.0 mg |
| Industrial alcohol | (150.0 mg) |

The captopril, microcristalline cellulose (Avicel 200), ascorbic acid and PEO are weighed and added to a mixer kneader. Dry mixing is carried out during 5 minutes, followed by a passage through 1.6 mm mesh sieve. The magnesium stearate is weighed and added with mixing in the dry state for 2 minutes. The tablets are obtained by compression in a rotary Frogerais MR 15 type machine.

Next, the methylcellulose (Methocel) is dissolved in the alcohol. The titanium dioxide is added to the solution followed by homogenization in an Ultra Turrax apparatus for 10 minutes. The tablets are spray coated with this suspension in a Glatt coater type coating apparatus.

EXAMPLE 7

The following composition is prepared:

| | |
|---|---|
| Verapamil.HCl | 240.0 mg |
| Lactose | 100.0 mg |
| PEO (MW = 1 000 000) | 200.0 mg |
| Magnesium stearate | 5.0 mg |
| Industrial alcohol | (200.0 mg) |

The Verapamil.HCl, lactose (available from the company HMS under reference 80 mesh) and the PEO are weighed and added to a mixer kneader followed by mixing in the dry state for 5 minutes. The alcohol is added to the mixture with further kneading for 5 minutes. Granulation is achieved by passage through a 1.6 mm mesh sieve. The granules are dried and passed through a 0.8 mm sieve. The magnesium stearate is weighed and added, with mixing in the dry state for 2 minutes. The tablets are obtained by compression in a rotary Frogerais MR 15 type machine.

EXAMPLE 8

The following composition is prepared:

| | |
|---|---|
| Diltiazem HCl | 180.0 mg |
| Lactose | 100.0 mg |
| PEO (MW = 1 500 000) | 160.0 mg |
| Magnesium stearate | 3.0 mg |
| Industrial alcohol | (150.0 mg) |

The diltiazem.HCl, lactose (HMS, 80 mesh) and PEO are weighed and added to a mixer kneader. Mixing is carried out in the dry state for 5 minutes. The alcohol is added to the mixture with mixing for 5 minutes. Granulation is achieved by passage through a 1.6 mm mesh sieve. The granules are dried and passed through a 0.8 mm mesh sieve. The magnesium stearate is weighed and added, followed by mixing in the dry state for 2 minutes. The tablets are obtained by compression in a rotary Frogerais MR 15 type machine.

EXAMPLE 9

The following composition is prepared:

| | |
|---|---|
| Oxybutynine.HCl | 15.0 mg |
| Microcrystalline cellulose | 75.0 mg |
| PEO (MW = 1 000 000) | 120.0 mg |
| Colloidal silicon dioxide | 1.5 mg |
| Magnesium stearate | 1.5 mg |
| Industrial alcohol | (110.0 mg) |

The oxybutynine.HCl, microcrystalline cellulose (Avicel PH 101) and PEO are weighed and added to a mixer kneader. Mixing in the dry state is performed for 5 minutes. The alcohol is added to the mixture with further mixing for 5 minutes. Granulation is achieved by passage through a 1.6 mm mesh sieve. The granules are dried. The colloidal silicon dioxide (Aerosil 200) is weighed and added followed by mixing in the dry state for 10 minutes and passage through a 0.8 mm mesh sieve. The magnesium stearate is weighed and added, with mixing in the dry state for 2 minutes. The tablets are obtained by compression in a rotary Frogerais MR 15 type machine.

EXAMPLE 10

The following composition was prepared:

| | |
|---|---|
| Core: | |
| Nifedipine | 60.0 mg |
| Microcrystalline cellulose | 100.0 mg |
| PEO (MW = 3 000 000) | 336.0 mg |
| Colloidal silicon dioxide | 2.5 mg |
| Magnesium stearate | 2.5 mg |
| Industrial alcohol | (150.0 mg) |
| Coating 1: | |
| Ammonio methacrylate copolymer type A | 160.0 mg |
| Hydroxy propyl methyl cellulose | 20.0 mg |
| Water | 30.0 g |
| Industrial alcohol | (150.0 mg) |
| Coating 2: | |
| Iron oxide | 2.0 mg |
| Titanium dioxide | 1.0 mg |
| Methylcellulose | 12.0 mg |
| Industrial alcohol | (150.0 mg) |

The method of preparing the core is identical to that described in Example 4.

Coating 1 is prepared as follows.

The hydroxy propyl methyl cellulose is weighed and dissolved in the water/alcohol mixture. The amminio methacrylate copolymer (USP XXIII, 12.5% solid available from Rohm Pharma, German under the commercial name Eudragit RL) is weighed and added followed by mixing. Coating is done in a Glatt coater type apparatus.

The method for preparing coating 2 and the application of the coating to the tablet obtained from the previous step are identical to those described in Example 4.

EXAMPLE 11

The following composition is prepared:

| | |
|---|---|
| Valacyclovir | 200.0 mg |
| PEO (MW = 300 000) | 700.0 mg |
| Magnesium stearate | 5.0 mg |
| Industrial alcohol | (260.0 mg |

The valacyclovir and PEO are weighed and added in a mixer kneader. Mixing in the dry state is performed for 5 minutes. Alcohol is added to the mixture, followed by mixing by 5 minutes. Granulation is achieved by passing through a sieve of 1.6 mm mesh. The granules are dried and are passed through a 0.8 mm mesh sieve. After weighing, magnesium stearate is added and mixing in the dry state is performed during 2 minutes. Tablets are obtained by compression using a Frogerais MR 15 type machine.

According to the general process disclosed in the previous examples, the following compositions are prepared, where the active ingredient is a crystalline powder.

EXAMPLE 12

The following composition was prepared:

| Core: | |
|---|---|
| Glipizide | 10.0 mg |
| PEO | 220.0 mg |
| Microcristalline cellulose | 55.0 mg |
| Hydroxy propyl methyl cellulose | 20.0 mg |
| Lactose | 50.0 mg |
| Sodium stearyl fumarate | 1.7 mg |
| Coating: | |
| Methacrylic acid copolymer | 10.0 mg |
| Polyethylene glycol | 2.0 mg |
| Talc | 2.5 mg |
| Silicon dioxide | 4.5 mg |

EXAMPLE 13

The following composition was prepared:

| Core: | |
|---|---|
| Glipizide | 10.0 mg |
| PEO | 220.0 mg |
| Microcristalline cellulose | 55.0 mg |
| Hydroxy propyl methyl cellulose | 20.0 mg |
| Lactose | 50.0 mg |
| Sodium stearyl fumarate | 1.7 mg |
| Coating: | |
| Ammonio methacrylate copolymer | 10.0 mg |
| Triethyl citrate | 3.0 mg |
| Polyethylene glycol | 1.0 mg |
| Hydroxypropylmethylcellulose | 7.0 mg |

EXAMPLE 14

The following composition was prepared:

| Core: | |
|---|---|
| Glipizide | 10.0 mg |
| PEO | 220.0 mg |
| Microcristalline cellulose | 55.0 mg |
| Hydroxy propyl methyl cellulose | 20.0 mg |
| Lactose | 50.0 mg |
| Sodium stearyl fumarate | 1.7 mg |
| Coating: | |
| Ammonio methacrylate copolymer | 10.0 mg |
| Lactose | 10.0 mg |
| Silicon dioxide | 4.0 mg |

EXAMPLE 15

The following composition was prepared:

| Core: | |
|---|---|
| Glipizide | 10.0 mg |
| PEO | 220.0 mg |
| Microcristalline cellulose | 55.0 mg |
| Hydroxy propyl methyl cellulose | 20.0 mg |
| Lactose | 50.0 mg |
| Sodium stearyl fumarate | 1.7 mg |
| Coating: | |
| 30% polyacrylate dispersion | 15.0 mg |
| Silicon dioxide | 6.0 mg |
| Talc | 2.0 mg |
| Hydroxypropylmethylcellulose | 6.0 mg |

EXAMPLE 16

The following composition was prepared:

| Core: | |
|---|---|
| Felodipine | 10.0 mg |
| PEO | 220.0 mg |
| Microcristalline cellulose | 55.0 mg |
| Hydroxy propyl methyl cellulose | 20.0 mg |
| Sodium stearyl fumarate | 1.5 mg |
| Coating: | |
| Methacrylic acid copolymer | 10.0 mg |
| Polyethylene glycol | 2.0 mg |
| Talc | 2.5 mg |
| Silicon dioxide | 4.5 mg |

EXAMPLE 17

The following composition was prepared:

| Core: | |
|---|---|
| Felodipine | 10.0 mg |
| PEO | 220.0 mg |
| Microcristalline cellulose | 55.0 mg |
| Hydroxy propyl methyl cellulose | 20.0 mg |
| Sodium stearyl fumarate | 1.5 mg |
| Coating: | |
| Ammonio methacrylate copolymer | 10.0 mg |
| Triethyl citrate | 3.0 mg |
| Polyethylene glycol | 1.0 mg |
| Hydroxypropylmethylcellulose | 7.0 mg |

EXAMPLE 18

The following composition was prepared:

| Core: | |
|---|---|
| Felodipine | 10.0 mg |
| PEO | 220.0 mg |
| Microcristalline cellulose | 55.0 mg |
| Hydroxy propyl methyl cellulose | 20.0 mg |
| Sodium stearyl fumarate | 1.5 mg |
| Coating: | |
| Ammonio methacrylate copolymer | 10.0 mg |
| Lactose | 10.0 mg |
| Silicon dioxide | 4.0 mg |

EXAMPLE 19

The following composition was prepared:

| Core: | |
|---|---|
| Felodipine | 10.0 mg |
| PEO | 220.0 mg |
| Microcrystalline cellulose | 55.0 mg |
| Hydroxy propyl methyl cellulose | 20.0 mg |
| Sodium stearyl fumarate | 1.5 mg |
| Coating: | |
| 30% polyacrylate dispersion | 15.0 mg |
| Silicon dioxide | 6.0 mg |
| Talc | 2.0 mg |
| Hydroxypropylmethylcellulose | 6.0 mg |

EXAMPLE 20

The following composition was prepared:

| Core: | |
|---|---|
| Isosorbide mononitrate | 60.0 mg |
| PEO | 100.0 mg |
| Microcristalline cellulose | 25.0 mg |
| low substituted Hydroxypropylcellulose | 5.0 mg |
| Glycerol behenate | 1.9 mg |
| Coating: | |
| Methacrylic acid copolymer | 10.0 mg |
| Polyethylene glycol | 2.0 mg |
| Talc | 2.5 mg |
| Silicon dioxide | 4.5 mg |

EXAMPLE 21

The following composition was prepared:

| Core: | |
|---|---|
| Isosorbide mononitrate | 60.0 mg |
| PEO | 100.0 mg |
| Microcristalline cellulose | 25.0 mg |
| low substituted Hydroxypropylcellulose | 5.0 mg |
| Glycerol behenate | 1.9 mg |
| Coating: | |
| Ammonio methacrylate copolymer | 5.0 mg |
| Triethyl citrate | 1.5 mg |
| Polyethylene glycol | 0.5 mg |
| Hydroxypropylmethylcellulose | 3.5 mg |

EXAMPLE 22

The following composition was prepared:

| Core: | |
|---|---|
| Isosorbide mononitrate | 60.0 mg |
| PEO | 100.0 mg |
| Microcristalline cellulose | 25.0 mg |
| low substituted Hydroxypropylcellulose | 5.0 mg |
| Glycerol behenate | 1.9 mg |
| Coating: | |
| Ammonio methacrylate copolymer | 5.0 mg |
| Lactose | 5.0 mg |
| Silicon dioxide | 2.0 mg |

EXAMPLE 23

The following composition was prepared:

| Core: | |
|---|---|
| Isosorbide mononitrate | 60.0 mg |
| PEO | 100.0 mg |
| Microcristalline cellulose | 25.0 mg |
| low substituted Hydroxypropylcellulose | 5.0 mg |
| Glycerol behenate | 1.9 mg |
| Coating: | |
| 30% polyacrylate dispersion | 7.5 mg |
| Silicon dioxide | 3.0 mg |
| Talc | 3.0 mg |
| Hydroxypropylmethylcellulose | 3.0 mg |

EXAMPLE 24

The following composition was prepared:

| Core: | |
|---|---|
| Carbidopa | 25.0 mg |
| Levodopa | 100.0 mg |
| Microcristalline cellulose | 20.0 mg |
| Povidone | 4.0 mg |
| Low substituted Hydroxypropylcellulose | 8.0 mg |
| PEO | 20.0 mg |
| Sodium stearyl fumarate | 1.7 mg |
| Coating: | |
| Methacrylic acid copolymer | 50.0 mg |
| Polyethylene glycol | 1.0 mg |
| Talc | 1.25 mg |
| Silicon dioxide | 2.25 mg |

EXAMPLE 25

The following composition was prepared:

| Core: | |
|---|---|
| Carbidopa | 25.0 mg |
| Levodopa | 100.0 mg |
| Microcristalline cellulose | 20.0 mg |
| Povidone | 4.0 mg |
| Low substituted Hydroxypropylcellulose | 8.0 mg |
| PEO | 20.0 mg |
| Sodium stearyl fumarate | 1.7 mg |
| Coating: | |
| Ammonio methacrylate copolymer | 5.0 mg |
| Triethyl citrate | 1.5 mg |
| Polyethylene glycol | 0.5 mg |
| Hydroxypropylmethylcellulose | 3.5 mg |

EXAMPLE 26

The following composition was prepared:

| Core: | |
|---|---|
| Carbidopa | 25.0 mg |
| Levodopa | 100.0 mg |
| Microcristalline cellulose | 20.0 mg |
| Povidone | 4.0 mg |
| Low substituted Hydroxypropylcellulose | 8.0 mg |
| PEO | 20.0 mg |
| Sodium stearyl fumarate | 1.7 mg |
| Coating: | |
| Ammonio methacrylate copolymer | 5.0 mg |
| Lactose | 5.0 mg |
| Silicon dioxide | 2.0 mg |

EXAMPLE 27

The following composition was prepared:

| Core: | |
|---|---|
| Carbidopa | 25.0 mg |
| Levodopa | 100.0 mg |
| Microcristalline cellulose | 20.0 mg |
| Povidone | 4.0 mg |
| Low substituted Hydroxypropylcellulose | 8.0 mg |
| PEO | 20.0 mg |
| Sodium stearyl fumarate | 1.7 mg |
| Coating: | |
| 30% polyacrylate dispersion | 7.5 mg |
| Silicon dioxide | 3.0 mg |
| Talc | 1.0 mg |
| Hydroxypropylmethylcellulose | 3.0 mg |

EXAMPLE 28

The following composition was prepared:

| Core: | |
|---|---|
| Pentoxiphylline | 400.0 mg |
| PEO | 150.0 mg |
| Povidone | 30.0 mg |
| Glycerol behenate | 6.0 mg |
| Coating: | |
| Methacrylic acid copolymer | 20.0 mg |
| Polyethylene glycol | 4.0 mg |
| Talc | 5.0 mg |
| Silicon dioxide | 9.0 mg |

EXAMPLE 29

The following composition was prepared:

| Core: | |
|---|---|
| Pentoxiphylline | 400.0 mg |
| PEO | 150.0 mg |
| Povidone | 30.0 mg |
| Glycerol behenate | 6.0 mg |
| Coating: | |
| Ammonio methacrylate copolymer | 20.0 mg |
| Triethyl citrate | 6.0 mg |
| Polyethylene glycol | 2.0 mg |
| Hydroxypropylmethylcellulose | 14.0 mg |

EXAMPLE 30

The following composition was prepared:

| Core: | |
|---|---|
| Pentoxiphylline | 400.0 mg |
| PEO | 150.0 mg |
| Povidone | 30.0 mg |
| Glycerol behenate | 6.0 mg |
| Coating: | |
| Ammonio methacrylate copolymer | 20.0 mg |
| Lactose | 20.0 mg |
| Silicon dioxide | 8.0 mg |

EXAMPLE 31

The following composition was prepared:

| Core: | |
|---|---|
| Pentoxiphylline | 400.0 mg |
| PEO | 150.0 mg |
| Povidone | 30.0 mg |
| Glycerol behenate | 6.0 mg |
| Coating: | |
| 30% polyacrylate dispersion | 30.0 mg |
| Silicon dioxide | 12.0 mg |
| Talc | 4.0 mg |
| Hydroxypropylmethylcellulose | 12.0 mg |

EXAMPLE 32

The following composition was prepared:

| Core: | |
|---|---|
| Nicardipine | 30.0 mg |
| PEO | 150.0 mg |
| Microcristalline cellulose | 30.0 mg |
| Povidone | 5.0 mg |
| Magnesium stearate | 2.0 mg |
| Coating: | |
| Methacrylic acid copolymer | 6.0 mg |
| Polyethylene glycol | 1.2 mg |
| Talc | 1.5 mg |
| Silicon dioxide | 2.7 mg |

EXAMPLE 33

The following composition was prepared:

| Core: | |
|---|---|
| Nicardipine | 30.0 mg |
| PEO | 150.0 mg |
| Microcristalline cellulose | 30.0 mg |
| Povidone | 5.0 mg |
| Magnesium stearate | 2.0 mg |
| Coating: | |
| Ammonio methacrylate copolymer | 6.0 mg |
| Triethyl citrate | 1.8 mg |
| Polyethylene glycol | 0.6 mg |
| Hydroxypropylmethylcellulose | 4.2 mg |

EXAMPLE 34

The following composition was prepared:

| Core: | |
|---|---|
| Nicardipine | 30.0 mg |
| PEO | 150.0 mg |
| Microcristalline cellulose | 30.0 mg |
| Povidone | 5.0 mg |
| Magnesium stearate | 2.0 mg |
| Coating: | |
| Ammonio methacrylate copolymer | 6.0 mg |
| Lactose | 6.0 mg |
| Silicon dioxide | 2.4 mg |

EXAMPLE 35

The following composition was prepared:

| Core: | |
|---|---|
| Nicardipine | 30.0 mg |
| PEO | 150.0 mg |
| Microcristalline cellulose | 30.0 mg |
| Povidone | 5.0 mg |
| Magnesium stearate | 2.0 mg |
| Coating: | |
| 30% polyacrylate dispersion | 9.0 mg |
| Silicon dioxide | 3.6 mg |
| Talc | 1.2 mg |
| Hydroxypropylmethylcellulose | 3.6 mg |

EXAMPLE 36

Carbamazepine Tablets

The following composition was prepared:

| Uncoated tablet (in mg) | |
|---|---|
| Carbamazepine | 400.00 |
| Polyox WSR N12 (MW = 1000000) | 200.00 |
| Lactose monohydrate | 81.00 |
| Polyvinylpyrrolidone (Plasdone K25) | 15.00 |

-continued

| Uncoated tablet (in mg) | |
|---|---|
| Purified water | 90.00 |
| Silica (Aerosil 200) | 7.00 |
| Sodium stearyl fumarate | 7.00 |

Preparation was as follows. The carbamazepine and lactose were introduced into a Stephan UMC5 blender, and the mixture was blended for 5 minutes dry. Plasdone K25 was dissolved in water and the solution was used to wet the powder. This was kneaded for 5 minutes. Granulation on a Erweka FGS oscillating granulator fitted with a 1.6 mm mesh grid was carried out. Next, drying on a fluidized bed down to a constant humidity value (value=1.8%) was carried out and this was followed by size grading on an oscillating granulator with a 0.8 mm mesh grid. Aerosil 200, after having first broken up any lumps, was added along with the sodium stearyl fumarate and the mixture was blended for 5 minutes. This was compressed on a Fette P2 rotary press provided with 12 mm diameter and 12 mm radius of curvature punches. The nominal mass of a tablet was 710 mg, and its average hardness was set to 12 kg.

The tablets were then given a surface film, using a conventional technique.

The tablets were then submitted to a dissolution test using the general method described in the third edition of the European Pharmacopoeia, with the following parameters:

| | |
|---|---|
| Method | basket |
| Rate of stirring | 150 rpm |
| Medium | water + 1% sodium lauryl sulfate |
| Volume of medium | 1000 ml |
| Assay | 258 nm on-line spectrophotometry |

The table below gives the results:

| Time (hours) | Fraction dissolved (%) |
|---|---|
| 0 | 0 |
| 0.5 | 3 |
| 1 | 9 |
| 2 | 21 |
| 4 | 43 |
| 6 | 60 |
| 8 | 73 |
| 12 | 90 |
| 18 | 100 |

EXAMPLE 37

Tablets of Nifedipine

The following formulation was prepared:

| uncoated tablet (in mg) | |
|---|---|
| Nifedipine | 60.00 |
| Polyox WSR N 60K (MW = 2000000) | 186.00 |
| Polyox WSR N 301 (MW = 4000000) | 156.00 |
| Microcrystalline cellulose (Avicel PH 101) | 99.00 |
| Purified water | 120.00 |

| uncoated tablet (in mg) | |
| --- | --- |
| Aerosil 200 | 2.5 |
| Magnesium stearate | 2.5 |

The method of preparation was as follows: the nifedipine and Avicel PH 101 were introduced into a Stephan UMC5 blender, and blending was performed dry for 5 minutes. The powder was wetted with water and blended for a further 5 minutes. The Polyox was added and blending was continued for a further 5 minutes. Granulation was carried out on an oscillating Erweka FGS granulator provided with an 1.6 mm mesh grid. Drying on a fluidized bed was carried down to a constant humidity (value 1.5%). The product was size-graded on an oscillating granulator with a 0.8 mm mesh grid. The Aerosil 200, after breaking up any possible lumps, and the magnesium stearate were added. Blending was continued for 5 minutes. The product was compressed on a rotary Fette P2 press provided with 11 mm diameter and 11 mm radius of curvature punches. The nominal mass of a tablet was 500 mg and its average hardness was set to 12 kg.

These tablets were then given a film coating using a conventional technique.

The tablets were subjected to a dissolution test using the following USP method:

| Method | basket |
| --- | --- |
| Rate of stirring | 150 rpm |
| Medium | water + 1, 25% Polysorbate 80 |
| Volume of medium | 1000 ml |
| Assay | 350 nm on-line spectrophotometry |

The results are given in the table below:

| Time (hours) | Fraction dissolved (%) |
| --- | --- |
| 0 | 0 |
| 4 | 9 |
| 12 | 28 |
| 16 | 38 |
| 20 | 48 |

EXAMPLE 38

Tablets of Verapamil

Following formulation was prepared

| uncoated tablet (in mg) | |
| --- | --- |
| Verapamil | 240 |
| Polyox WSR N12 (MW = 1000000) | 60 |
| Lactose | 300 |
| Plasdone K25 | 14 |
| Purified water | 90 |
| Aerosil 200 | 2 |
| Sodium stearyl fumarate | 4 |

The manner of preparation was as follows. Verapamil and lactose were introduced into a Stephan UMC5 blender, and blending was carried out for 5 minutes. The Plasdone K25 was dissolved in water, and the powder was wetted with this solution. Blending was continued for 5 minutes. Next, the Polyox was added and blending was continued for a further 5 minutes. Granulation was performed on an oscillating Erweka FGS granulator provided with an 1.6 mm mesh grid. The product was dried on a fluidized bed down to a constant humidity (value 2.3%). Size-grading was carried out on an oscillating granulator with an 0.8 mm mesh grid. The Aerosil 200, any lumps previously being broken up, and the sodium stearyl fumarate were added. Blending was continued for 5 minutes. Next, the powder was compressed on a rotary Fette P2 press provided with 12 mm diameter and 12 mm radius of curvature punches. The nominal mass of the tablet was 620 mg and its average hardness was set to 12 kg.

These tablets were then given a film coating using a conventional formulation.

The tablets were subjected to a dissolution test using the following USP method:

| Method | basket |
| --- | --- |
| Rate of stirring | 100 rpm |
| Medium | buffer pH 6,8 |
| Volume of medium | 1000 ml |
| Assay | 274 nm on-line spectrophotometry |

The results are given in the table below:

| Time (hours) | fraction dissolved (%) |
| --- | --- |
| 0 | 0 |
| 1 | 17 |
| 2 | 30 |
| 4 | 50 |
| 6 | 72 |
| 8 | 92 |
| 12 | 100 |

EXAMPLE 39

Tablets of Diltiazem

The following formulation was prepared:

| Uncoated tablet (mg) | |
| --- | --- |
| Diltiazem | 60.00 |
| Polyox WSR N 303 (MW = 5000000) | 50.00 |
| Avicel PH 101 | 30.00 |
| Purified water | 20.00 |
| Aerosil 200 | 1.00 |
| Sodium stearyl fumarate | 2.00 |

The method of preparation was as follows. The diltiazem and Avicel PH 101 were introduced into a Stephen UMC5 blender and blending was carried out dry for 5 minutes. Next, the powder was wetted with water and blended for a further 5 minutes. Then, the Polyox was added and blending was continued for a further 5 minutes. The product was granulated on an oscillating Erweka FGS granulator provided with an 1.6 mm mesh grid. The product was dried on a fluidized bed down to a constant humidity (value 2.3%). Size grading was carried out on an oscillating granulator with an 0.8 mm mesh grid. Next, the Aerosil 200 was added after previously breaking up any possible lumps, together with the sodium stearyl fumarate and blending was continued for 5 minutes. Compression was carried out on a rotary Fette P2 press provided with 6 mm diameter and 6 mm radius of curvature punches. The nominal mass of a tablet was 143 mg and its average hardness was set to 8 kg.

The tablets were then given a film coating using a conventional formulation.

The tablets were subjected to a dissolution test using the following USP method:

| Method | basket |
|---|---|
| Rate of stirring | 100 rpm |
| Medium | buffer pH 6,8 |
| Volume of medium | 1000 ml |
| Assay | 274 nm on-line spectrophotometry |

The results are given in the table below:

| Time (hours) | fraction dissolved (%) |
|---|---|
| 0 | 0 |
| 0.5 | 5 |
| 1 | 12 |
| 2 | 23 |
| 4 | 44 |
| 6 | 60 |
| 8 | 72 |
| 12 | 91 |
| 18 | 100 |

EXAMPLE 40

Tablets of Glipizide

The following formulation was prepared:

| Uncoated tablet (in mg) | |
|---|---|
| Glipizide | 400.00 |
| Polyox WSP N60 K (MW = 2000000) | 200.00 |
| Avicel PH 101 | 80.00 |
| Plasdone K25 | 6.00 |
| Purified water | 50.00 |
| Aerosil 200 | 2.00 |
| Sodium stearyl fumarate | 2.00 |

The method of preparation was as follows. The glipizide and Avicel were introduced into a Stephan UMC5 blender and blending was carried out dry for 5 minutes. The Plasdone K25 was dissolved in water and the powder was wetted with this solution followed by blending for 5 minutes. Then, the Polyox was added and blending was continued for a further 5 minutes. The product was granulated on an oscillating Erweka FGS granulator provided with a 1.6 mm mesh grid. The product was dried on a fluidized bed down to a constant humidity (value 1.8%). Size grading was carried out on an oscillating granulator with an 0.8 mm mesh grid. Next, the Aerosil 200 was added after previously breaking up any possible lumps, together with the sodium stearyl fumarate and blending was continued for 5 minutes. Compression was carried out on a rotary Fette P2 press provided with 10 mm diameter and 10 mm radius of curvature punches. The nominal mass of a tablet was 300 mg and its average hardness was set to 9 kg.

These tablets were then given a gastro-resistant film coating using a conventional formulation.

These tablets were subjected to a dissolution test using the following USP method of example 1:

| Method | paddle + sinker |
|---|---|
| Rate of stirring | 200 rpm |
| Medium | HCl 0,1N followed by buffer pH 6,8 |
| Volume of medium | 1000 ml |
| Assay | 258 nm on-line spectrophotometry |

The results are given in the table below:

| time (hours) | fraction dissolved (%) |
|---|---|
| 0 | 0 |
| 1 | 0 |
| 2 | 2 |
| 4 | 12 |
| 6 | 27 |
| 8 | 43 |
| 12 | 72 |
| 18 | 85 |

EXAMPLE 41

Tablets of Pentoxiphylline

The following formulation was prepared:

| Uncoated tablet (in mg) | |
|---|---|
| Pentoxiphylline | 400.00 |
| Polyox WSR N12 K (MW = 1000000) | 200.00 |
| Plasdone | 22.00 |
| Purified water | 180.00 |
| Aerosil 200 | 3.00 |
| Sodium stearyl fumarate | 5.00 |

The method of preparation was as follows. The pentoxiphylline is introduced into a Stephan UMC5 blender and blending was carried out dry for 5 minutes. The Plasdone K25 was dissolved in water and the powder was wetted with this solution followed by blending for 5 minutes. Then, the Polyox was added and blending was continued for a further 5 minutes. The product was granulated on an oscillating Erweka FGS granulator provided with an 1.6 mm mesh grid. The product was dried on a fluidized bed down to a constant humidity (value 1.7%). Size grading was carried out on an oscillating granulator with an 0.8 mm mesh grid. Next, the Aerosil 200 was added after previously breaking up any possible lumps, together with the sodium stearyl fumarate and blending was continued for 5 minutes. Compression was carried out on a rotary Fette P2 press provided with 12 mm diameter and 12 mm radius of curvature punches. The nominal mass of a tablet was 630 mg and its average hardness was set to 12 kg.

These tablets were then given a film coating using a conventional formulation.

The tablets were subjected to a dissolution test using the following USP method:

| Method | basket |
|---|---|
| Rate of stirring | 100 rpm |
| Medium | buffer pH 6,8 |
| Volume of medium | 1000 ml |
| Assay | 246 nm on-line spectrophotometry |

The results are given in the table below:

| Time (hours) | fraction dissolved (%) |
|---|---|
| 0 | 0 |
| 0.5 | 9 |
| 1 | 14 |
| 2 | 22 |
| 4 | 34 |
| 6 | 44 |
| 8 | 53 |
| 12 | 70 |
| 18 | 90 |

EXAMPLE 42

Tablets of Cefaclor

The following formulation was prepared:

| Uncoated tablet (in mg) | |
|---|---|
| Cefaclor | 400.00 |
| Polyox coagulant (MW = 5000000) | 200.00 |
| Avicel PH 101 | 59.00 |
| Purified water | 100.00 |
| Aerosil 200 | 7.00 |
| Magnesium stearate | 7.00 |

The method of preparation was as follows. The Cefaclor and Avicel PH 101 were introduced into a Stephan UMC5 blender and blending was carried out dry for 5 minutes. Next, the powder was wetted with water and blended for 5 minutes. Then, the Polyox was added and blending was continued for a further 5 minutes. The product was granulated on an oscillating Erweka FGS granulator provided with an 1.6 mm mesh grid. The product was dried on a fluidized bed down to a constant humidity. Size grading was carried out on an oscillating granulator with an 0.8 mm mesh grid. Next, the Aerosil 200 was added after previously breaking up any possible lumps, together with the magnesium stearate and blending was continued for 5 minutes. Compression was carried out on a rotary Fette P2 press provided with oblong 18.5 mm long and 6.5 mm wide punches. The nominal mass of a tablet was 670 mg.

The tablets were then given a film coating using a conventional formulation.

EXAMPLE 43

Tablets of Itraconazole

The following formulation was prepared:

| Uncoated tablet (in mg) | |
|---|---|
| Itraconazole | 100.00 |
| Polyox WSR N10 (MW = 100,000) | 100.00 |
| Avicel PH 101 | 30.00 |
| Purified water | 72.00 |
| Aerosil 200 | 1.00 |
| Magnesium stearate | 1.00 |

The method of preparation was as follows. The itraconazole and Avicel PH 101 were introduced into a Stephan UMC5 blender and blending was carried out dry for 5 minutes. Next, the powder was wetted with water and blended for a further 5 minutes. Then, the Polyox was added and blending was continued for a further 5 minutes. The product was granulated on an oscillating Erweka FGS granulator provided with an 1.6 mm mesh grid. The product was dried on a fluidized bed down to a constant humidity (value 2.1%). Size grading was carried out on an oscillating granulator with an 0.8 mm mesh grid. Next, the Aerosil 200 was added after previously breaking up any possible lumps, together with the magnesium stearate and blending was continued for 5 minutes. Compression was carried out on a rotary Fette P2 press provided with 8 mm diameter and 7 mm radius of curvature punches. The nominal mass of a tablet was 232 mg and its average hardness was set to 9 kg.

EXAMPLE 44

Tablets of Venlafaxine

The following formulation was prepared:

| Uncoated tablet (in mg) | |
|---|---|
| Venlafaxine (hydrochloride) | 106.00 |
| Polyox WSR N 750 (MW = 300,000) | 140.00 |
| Avicel PH 101 | 40.00 |
| Purified water | 65.00 |
| Aerosil 200 | 1.00 |
| Magnesium stearate | 1.00 |

The method of preparation was as follows. The venlafaxine hydrochloride and Avicel PH 101 were introduced into a Stephen UMC5 blender and blending was carried out dry for 5 minutes. Next, the powder was wetted with water and blended for a further 5 minutes. Then, the Polyox was added and blending was continued for a further 5 minutes. The product was granulated on an oscillating Erweka FGS granulator provided with an 1.6 mm mesh grid. The product was dried on a fluidized bed down to a constant humidity. Size grading was carried out on an oscillating granulator with an 0.8 mm mesh grid. Next, the Aerosil 200 was added after previously breaking up any possible lumps, together with the magnesium stearate and blending was continued for 5 minutes. Compression was carried out on a rotary Fette P2 press provided with 10 mm diameter and 10 mm radius of curvature punches. The nominal mass of a tablet was 288 mg and its average hardness was set to 9 kg.

EXAMPLE 45

Tablets of Quinapril

| Uncoated tablet (in mg) | |
| --- | --- |
| Quinapril | 20.00 |
| Polyox WSR N750 (MW = 300,000) | 200.00 |
| Avicel PH 101 | 60.00 |
| Purified water | 100.00 |
| Aerosil 200 | 1.00 |
| Sodium stearyl fumarate | 1.00 |

The method of preparation was as follows. The Quinapril and Avicel PH 101 were introduced into a Stephan UMC5 blender and blending was carried out dry for 5 minutes. Next, the powder was wetted with water and blending continued a further 5 minutes. Then, the Polyox was added and blending was continued for a further 5 minutes. The product was granulated on an oscillating Erweka FGS granulator provided with an 1.6 mm mesh grid. The product was dried on a fluidized bed down to a constant humidity (value 1.6%). Size grading was carried out on an oscillating granulator with an 0.8 mm mesh grid. Next, the Aerosil 200 was added after previously breaking up any possible lumps, together with the sodium stearyl fumarate and blending was continued for 5 minutes. Compression was carried out on a rotary Fette P2 press provided with 9 mm diameter and 9 mm radius of curvature punches The nominal mass of a tablet was 282 mg and its average hardness was set to 9 kg.

the tablets were then given a film coating using a conventional formulation.

EXAMPLE 46

Tablets of Felodipine and Enalapril

The following formulation was prepared:

| Uncoated tablet (in mg) | |
| --- | --- |
| Felodipine | 10.00 |
| Enalapril (maleate) | 5.00 |
| Polyox WSR N 750 (MW = 300,000) | 250.00 |
| Avicel PH 101 | 101.00 |
| Purified water | 45.00 |
| Aerosil 200 | 2.00 |
| Sodium stearyl fumarate | 2.00 |

The method of preparation was as follows. The felodipine, enalapril and Avicel PH 101 were introduced into a Stephan UMC5 blender and blending was carried out dry for 5 minutes. The powder was wetted with water and blended for a further 5 minutes. Then, the Polyox was added and blending was continued for a further 5 minutes. The product was granulated on an oscillating Erweka FGS granulator provided with an 1.6 mm mesh grid. The product was dried on a fluidized bed down to a constant humidity (value 1.2%). Size grading was carried out on an oscillating granulator with an 0.8 mm mesh grid. The Aerosil 200 was added after previously breaking up any possible lumps, together with the sodium stearyl fumarate and blending was continued for 5 minutes. Compression was carried out on a rotary Fette P2 press provided with 10 mm diameter and 10 mm radius of curvature punches. The nominal mass of a tablet was 370 mg and its average hardness was set to 10 kg.

These tablets were then given a film coating using a conventional formulation.

EXAMPLE 47

Tablets of Levodopa and Carbidopa

The following formulation was prepared:

| Uncoated tablet (in mg) | |
| --- | --- |
| Levodopa | 200.00 |
| Carbidopa | 55.00 |
| Polyox WSR N 80 (MW = 200000) | 60.00 |
| Purified water | 45.00 |
| Aerosil 200 | 1.5 |
| Sodium stearyl fumarate | 3.5 |

The method of preparation was as follows. The levodopa, carbidopa were introduced into a Stephan UMC5 blender and blending was carried out dry for 5 minutes. The powder was wetted with water and blended for a further 5 minutes. Then, the Polyox was added and blending was continued for a further 5 minutes. The product was granulated on an oscillating Erweka FGS granulator provided with an 1.6 mm mesh grid. The product was dried on a fluidized bed down to a constant humidity. Size grading was carried out on an oscillating granulator with an 0.8 mm mesh grid. The Aerosil 200 was added after previously breaking up any possible lumps, together with the sodium stearyl fumarate and blending was continued for 5 minutes. Compression was carried out on a rotary Fette P2 press provided with 9 mm diameter and 9 mm radius of curvature punches. The nominal mass of a tablet was 320 mg and its average hardness was set to 10 kg.

These tablets were then given a film coating using a conventional formulation.

EXAMPLE 48

Tablets of Felodipine

The following formulation was prepared:

| Uncoated tablet (in mg) | |
| --- | --- |
| Felodipine | 10.00 |
| Polyox WSR N 750 (MW = 300,000) | 300.00 |
| Avicel PH 101 | 101.00 |
| Purified water | 45.00 |
| Aerosil 200 | 2.00 |
| Sodium stearyl fumarate | 2.00 |

The method of preparation was as follows. The felodipine and Avicel PH 101 were introduced into a Stephan UMC5 blender and blending was carried out dry for 5 minutes. The powder was wetted with water and blended for a further 5 minutes. Then, the Polyox was added and blending was continued for a further 5 minutes. The product was granulated on an oscillating Erweka FGS granulator provided with an 1.6 mm mesh grid. The product was dried on a fluidized bed down to a constant humidity. Size grading was carried out on an oscillating granulator with an 0.8 mm mesh grid. The Aerosil 200 was added after previously breaking up any possible lumps, together with the sodium stearyl fumarate and blending was continued for 5 minutes. Compression was carried out on a rotary Fette P2 press provided with 11 mm diameter and 11 mm radius of curvature punches. The nominal mass of a tablet was 415 mg and its average hardness was set to 11 kg.

These tablets were then given a film coating using a conventional formulation.

EXAMPLE 49

Tablets of Nicardipine

Following formulation was prepared

| uncoated tablet (in mg) | |
| --- | --- |
| Nicardipine | 50 |
| Polyox WSR N 60 K (MW = 2000000) | 110 |
| Avicel PH 101 | 46 |
| Plasdone K29–32 | 6 |
| Purified water | 35 |
| Aerosil 200 | 1 |
| Sodium stearyl fumarate | 2 |

The manner of preparation was as follows. Nicardipine and Avicel were introduced into a Stephan UMC5 blender, and blending was carried out for 5 minutes. The Plasdone K29–32 was dissolved in water, and the powder was wetted with this solution. Blending was continued for 5 minutes. Next, the Polyox was added and blending was continued for a further 5 minutes. Granulation was performed on an oscillating Erweka FGS granulator provided with an 1.6 mm mesh grid. The product was dried on a fluidized bed down to a constant humidity. Size-grading was carried out on an oscillating granulator with an 0.8 mm mesh grid. The Aerosil 200, any lumps previously being broken up, and the sodium stearyl fumarate were added. Blending was continued for 5 minutes. Next, the powder was compressed on a rotary Fette P2 press provided with 8 mm diameter and 8 mm radius of curvature punches. The nominal mass of the tablet was 215 mg and its average hardness was set to 8 kg.

These tablets were then given a film coating using a conventional formulation.

EXAMPLE 50

Tablets of Nisoldipine

Following formulation was prepared

| uncoated tablet (in mg) | |
| --- | --- |
| Nisoldipine | 10 |
| Polyox WSR N 60 K (MW = 2000000) | 180 |
| Avicel PH 101 | 61 |
| Plasdone K29-32 | 10 |
| Purified water | 55 |
| Aerosil 200 | 1.2 |
| Sodium stearyl fumarate | 2.8 |

The manner of preparation was as follows. Nisoldipine and Avicel were introduced into a Stephan UMC5 blender, and blending was carried out for 5 minutes. The Plasdone K29–32 was dissolved in water, and the powder was wetted with this solution. Blending was continued for 5 minutes. Next, the Polyox was added and blending was continued for a further 5 minutes. Granulation was performed on an oscillating Erweka FGS granulator provided with an 1.6 mm mesh grid. The product was dried on a fluidized bed down to a constant humidity. Size-grading was carried out on an oscillating granulator with an 0.8 mm mesh grid. The Aerosil 200, any lumps previously being broken up, and the sodium stearyl fumarate were added. Blending was continued for 5 minutes. Next, the powder was compressed on a rotary Fette P2 press provided with 9 mm diameter and 9 mm radius of curvature punches. The nominal mass of the tablet was 265 mg and its average hardness was set to 10 kg.

These tablets were then given a film coating using a conventional formulation.

EXAMPLE 51

Tablets of Metoprolol

Following formulation was prepared

| uncoated tablet (in mg) | |
| --- | --- |
| Metoprolol | 200 |
| Polyox WSR N 301 (MW = 4000000) | 300 |
| Avicel PH 101 | 54 |
| Plasdone K29-32 | 8 |
| Purified water | 60 |
| Aerosil 200 | 3 |
| Sodium stearyl fumarate | 5 |

The manner of preparation was as follows. Metoprolol and Avicel were introduced into a Stephan UMC5 blender, and blending was carried out for 5 minutes. The Plasdone K29–32 was dissolved in water, and the powder was wetted with this solution. Blending was continued for 5 minutes. Next, the Polyox was added and blending was continued for a further 5 minutes. Granulation was performed on an oscillating Erweka FGS granulator provided with an 1.6 mm mesh grid. The product was dried on a fluidized bed down to a constant humidity. Size-grading was carried out on an oscillating granulator with an 0.8 mm mesh grid. The Aerosil 200, any lumps previously being broken up, and the sodium stearyl fumarate were added. Blending was continued for 5 minutes. Next, the powder was compressed on a rotary Fette P2 press provided with 12 mm diameter and 12 mm radius of curvature punches. The nominal mass of the tablet was 570 mg and its average hardness was set to 18 kg.

These tablets were then given a film coating using a conventional formulation.

EXAMPLE 52

Tablets of Isradipine

The following formulation was prepared:

| uncoated tablet (in mg) | |
| --- | --- |
| Isradipine | 60.00 |
| Polyox WSR N 60K (MW = 2000000) | 150.00 |
| Polyox WSR N 301 (MW = 4000000) | 150.00 |
| Avicel PH 101 | 99.00 |
| Purified water | 120.00 |
| Aerosil 200 | 2.5 |
| Magnesium stearate | 2.5 |

The method of preparation was as follows: the isradipine and Avicel PH 101 were introduced into a Stephan UMC5 blender, and blending was performed dry for 5 minutes. The powder was wetted with water and blended for a further 5 minutes. The Polyox was added and blending was continued for a further 5 minutes. Granulation was carried out on an oscillating Erweka FGS granulator provided with an 1.6 mm mesh grid. Drying on a fluidized bed was carried down to a constant humidity. The product was size-graded on an oscillating granulator with a 0.8 mm mesh grid. The Aerosil 200, after breaking up any possible lumps, and the magnesium stearate were added. Blending was continued for 5 minutes. The product was compressed on a rotary Fette P2 press provided with 11 mm diameter and 11 mm radius of curvature punches. The nominal mass of a tablet was 464 mg and its average hardness was set to 12 kg.

These tablets were then given a film coating using a conventional technique.

What is claimed is:

1. A process for preparing a solid pharmaceutical composition comprising, by weight based on the total weight of the composition:
   (a) from 1 to 70% of active ingredient which is not in an amorphous form;
   (b) from 10 to 95% of polyethylene oxide;
   (c) the balance consisting of conventional additives, comprising the steps of:
      (i) mixing said active ingredient and optionally one or several additives with an aqueous solution for a sufficient period of time; then
      (ii) adding the PEO, and mixing for a sufficient period of time.

2. The process according to claim 1, in which step (i) of mixing with the aqueous solution is carried out in the presence of excess liquid.

3. The process according to claim 1, in which said aqueous solution consists of water, and, optionally, water-soluble additives.

4. The process according to claim 1, further comprising a granulation step.

5. The process according to claim 2, further comprising a granulation step.

6. The process according to claim 4, in which said granulation step is carried out on a screen of suitable mesh size.

7. The process according to claim 5, in which said granulation step is carried out on a screen of suitable mesh size.

8. The process according to claim 1, additionally comprising a drying step.

9. The process according to claim 2, additionally comprising a drying step.

10. The process according to claim 4, additionally comprising a drying step.

11. The process according to claim 5, additionally comprising a drying step.

12. The process according to claim 1, further comprising a compression step.

13. The process according to claim 7, in which said compression step is preceded by a step in which additives are added and blended.

14. The process according to claim 2, further comprising a compression step.

15. The process according to claim 4, further comprising a compression step.

16. The process according to claim 5, further comprising a compression step.

17. The process according to claim 1, comprising the steps of:
   (i) mixing, for a sufficient period of time, active ingredient and, optionally, one of several additives, with said aqueous solution; then
   (ii) adding PEO and mixing for a sufficient period of time;
   (iii) granulating the mixture obtained from step (ii);
   (iv) drying granules thus formed for a sufficient period of time;
   (vi) optionally, adding one or several additives, and mixing in the dry state for a sufficient period of time;
   (vii) compressing the mixture obtained from the preceding step into a tablet.

18. The process according to claim 17, in which step (i) of mixing with the aqueous solution is carried out in the presence of excess liquid.

* * * * *